United States Patent
Hess

(10) Patent No.: US 12,329,988 B1
(45) Date of Patent: Jun. 17, 2025

(54) APPARATUS AND METHOD FOR RADIATION THERAPY

(71) Applicant: CureRays, Inc., Atlanta, GA (US)

(72) Inventor: Clayton Hess, Sacramento, CA (US)

(73) Assignee: CureRays, Inc., Atlanta, GA (US)

( * ) Notice: Subject to any disclaimer, the term of this patent is extended or adjusted under 35 U.S.C. 154(b) by 0 days.

(21) Appl. No.: 18/968,576

(22) Filed: Dec. 4, 2024

Related U.S. Application Data

(60) Provisional application No. 63/611,772, filed on Dec. 19, 2023.

(51) Int. Cl.
*A61N 5/10* (2006.01)

(52) U.S. Cl.
CPC ......... *A61N 5/1067* (2013.01); *A61N 5/1077* (2013.01); *A61N 2005/1094* (2013.01)

(58) Field of Classification Search
None
See application file for complete search history.

(56) References Cited

U.S. PATENT DOCUMENTS

| | | | |
|---|---|---|---|
| 2010/0329413 A1* | 12/2010 | Zhou | A61N 5/10 378/65 |
| 2017/0368373 A1* | 12/2017 | Sahadevan | A61N 5/1067 |
| 2018/0154183 A1* | 6/2018 | Sahadevan | A61M 1/3615 |
| 2020/0289851 A1* | 9/2020 | Dilmanian | A61N 5/1042 |
| 2024/0355498 A1* | 10/2024 | Jung | A61N 5/1077 |

\* cited by examiner

*Primary Examiner* — Hoon K Song
(74) *Attorney, Agent, or Firm* — FisherBroyles LLC; Glen L Nuttall

(57) ABSTRACT

A radiotherapy system is configured to receive an open-field X-ray beam from a superficial radiotherapy machine and direct the beam through a grid module configured to spatially fractionate the open-field beam into a group of spaced-apart microbeams. A patient applicator defines an enclosed space having a patient support surface for supporting a target body part. A beam receiver of the patient applicator receives the group of microbeams directed at the target body part on the support surface. The enclosed space is defined by a wall structure comprising shielding sufficient to absorb the radiation emitted by the superficial radiotherapy machine. The patient applicator 80 can be portable, and the superficial radiotherapy machine can be wheeled.

12 Claims, 14 Drawing Sheets

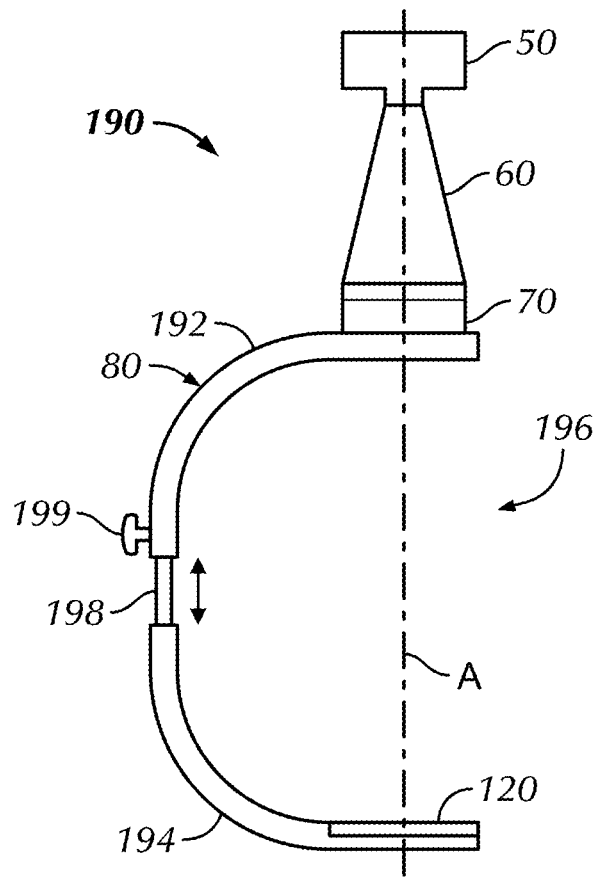
FIG. 8
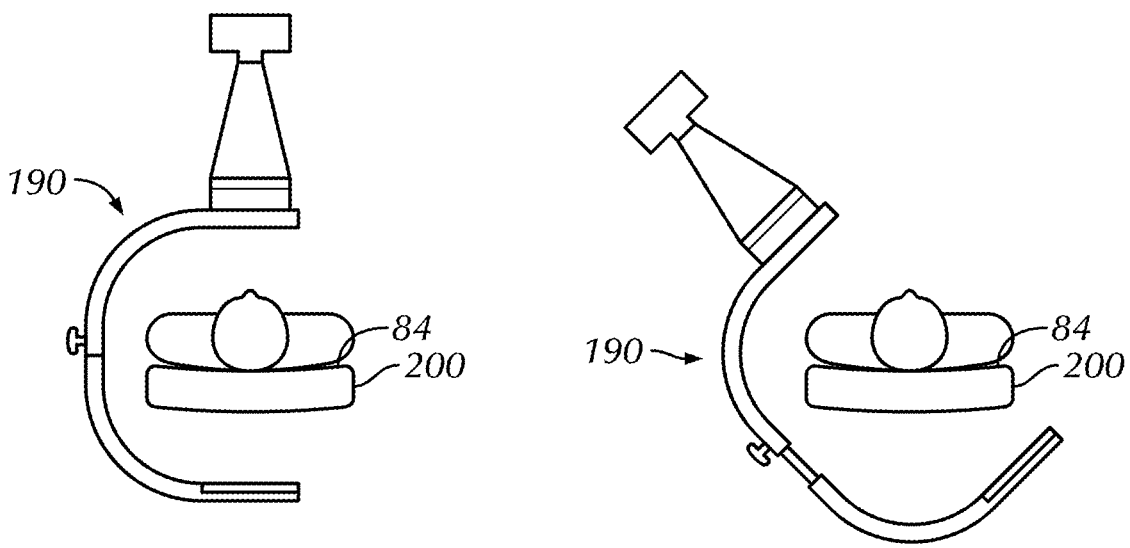
FIG. 9A  FIG. 9B

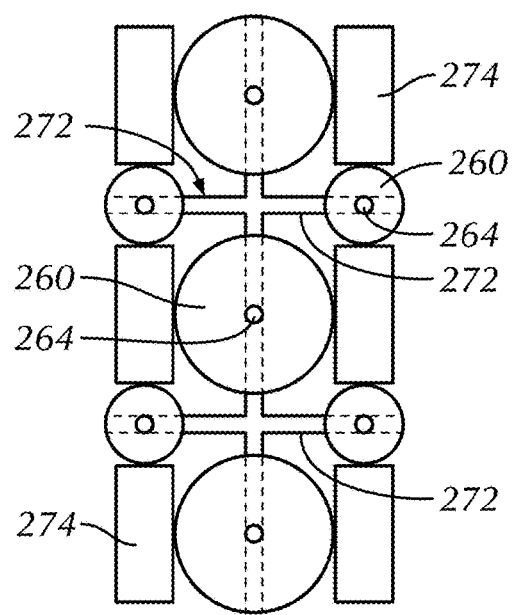
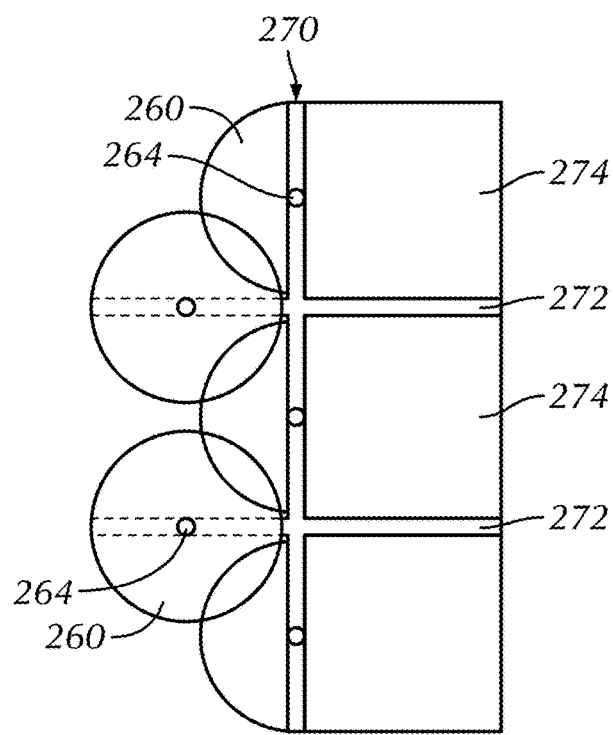
FIG. 22
FIG. 23

APPARATUS AND METHOD FOR RADIATION THERAPY

CROSS-REFERENCE TO RELATED APPLICATIONS

The application claims priority to U.S. Provisional Application No. 63/611,772, filed Dec. 19, 2023, the entirety of which is hereby incorporated by reference.

BACKGROUND

The present disclosure relates to the field of radiation therapy, also referred to as radiotherapy, and more specifically to radiotherapy using kilovoltage or orthovoltage-level radiation.

Radiation therapy is commonly used in the treatment of cancers. Lower-energy radiation-often referred to as "superficial radiation"-employs relatively low-energy photons energized at the orthovoltage-level (100-500 kV) and kilovoltage-level (<100 kV). Such lower-energy radiation typically is readily absorbed by patient tissue, and thus much of the dose is absorbed by the skin and adjacent tissues within millimeters or just a few centimeters of the skin surface. Delivery of a large dose of superficial radiation to a deep-seated cancer would thus also involve delivering extensive, oft-damaging radiation to skin and adjacent tissues. As such, kilovoltage-level radiation is typically used only for superficial treatments, such as non-melanoma skin cancers, keloid scars, and the like. An advantage of using superficial radiation in therapy, however, is that it has relatively low power requirements and relatively low radiation exposure, and shielding requirements are correspondingly low. Further, superficial radiation therapy (SRT) systems can be relatively small, often are mobile, and can also employ mobile containment structures to provide adequate shielding.

Due to the limiting characteristics of superficial radiation therapy using such orthovoltage and kilovoltage x-rays, most radiation therapy for subcutaneous cancers employs photons energized to the megavoltage level (typically 4-18 MV). Megavoltage-level radiation therapy typically involves large, high-powered machinery including linear accelerators that must be permanently installed in specialized rooms often referred to as bunkers or vaults. Such specialized rooms must be constructed with extensive shielding in order to contain the high-powered megavoltage radiation. Thus, such systems require substantial capital, physical, and real estate investment, yet have limited versatility and accessibility. As such, megavoltage-level radiation therapy treatments tend to be extremely expensive, limited in availability, and inconvenient.

Spatially fractionated radiation therapy (SFRT) involves applying a non-uniform dose of radiation to a tumor or other treatment target tissue. A technique of SFRT known as grid therapy involves dividing an open-field X-ray beam into an array of multiple pencil beams, or microbeams. Such grid therapy has been found to have reduced toxicity to tissues surrounding the target tissue, including skin.

SUMMARY

The present disclosure presents apparatus and methods that improve radiotherapy using kilovoltage- and/or orthovoltage-level beam energy. Radiation therapy is a known effective treatment for cancerous tumors, and has shown promise as an effective treatment of inflammation disorders, including arthritis, and even treating COVID-19-induced inflammation in the lungs. Superficial radiotherapy systems use comparatively low-energy beams and thus have relatively low shielding requirements, and can be easily mobilized. Although superficial radiation is known to have relatively high rates of skin absorption, skin toxicity can be minimized by spatially fractionating the beam, such as by using a grid. Also, taking multiple therapy passes from different directions limit the radiation dose absorbed by any one zone of skin to a single pass, but apply radiation from all therapy passes to the target tissue.

In accordance with one embodiment, the present specification comprises a method of performing radiotherapy upon a subcutaneous target tissue. The method includes directing a first open-field beam of X-rays having an energy less than 500 KV into a grid module, the grid module configured to spatially fractionate the first open-field beam into a first group of microbeams. The method further includes directing the first group of microbeams into a patient applicator, the patient applicator having a wall structure defining an interior space and a patient support surface configured to support a target body part. Another step includes directing the first group of microbeams at the target body part so that radiation from the first group of microbeams penetrates and is partially absorbed by a first skin zone of the target body part and is also partially absorbed by the target tissue, and then repositioning one or more of the grid module and target body part. After repositioning, the method includes directing a second open-field beam of X-rays having an energy less than 500 KV into the grid module so that the second open-field beam is spatially fractionated into a second group of microbeams, directing the second group of microbeams into the patient applicator, and directing the second group of microbeams at the target body part so that radiation from the second group of microbeams penetrates and is partially absorbed by a second skin zone of the target body part and is also partially absorbed by the target tissue. The first skin zone is spaced from the second skin zone.

In one embodiment, repositioning comprises moving a portion of the patient applicator while leaving the target body part and patient support surface static.

Another embodiment comprises actively modifying the grid module prior to directing the second open-field beam so that the second group of microbeams is configured differently than the first group of microbeams.

Still another embodiment comprises obtaining an X-ray image of the target tissue prior to directing the first open-field beam, determining a first perimeter shape of the target tissue and adjusting the grid module so that the first group of microbeams has an outer perimeter shape approximating the first perimeter shape.

Another such embodiment comprises obtaining an X-ray image of the target tissue after the repositioning, determining a second perimeter shape of the target tissue and adjusting the grid module so that the second group of microbeams has an outer perimeter shape approximating the second perimeter shape.

In accordance with another embodiment the present specification provides a radiotherapy device, comprising an applicator interface configured to attach to a head of a superficial radiotherapy machine and positioned so as to receive an open-field X-ray beam from the head, and a grid module configured to attach to the applicator interface and configured to receive the open-field X-ray beam from the applicator interface. The grid module can comprise a filter member configured to spatially fractionate the open-field X-ray beam into a group of microbeams having a beam axis. A patient applicator can be attached to the grid module, the patient applicator comprising an applicator body having a first portion that extends in a direction transverse to the beam axis, a second portion that extends in a direction generally parallel to the beam axis, and a third portion that extends in a direction transverse to the beam axis, the third portion having a distal end that intersects the beam axis and is spaced from the first portion. The third portion can comprise an imaging panel.

In some such embodiments the patient applicator is configured so that a distance between the distal end of the third portion and the first portion can be selectively decreased.

In another embodiment the present specification provides a radiotherapy device, comprising a wheeled base and a plurality of shielded modules supported on the base. Each of the shielded modules comprise: a tubular member having a generally circular cross-section and a beam receiver extending through a wall of the tubular member. The tubular member is configured to selectively engage a grid module at and adjacent the beam receiver. The grid module can comprise at least one filter member configured to spatially fractionate an input open-field X-ray beam and output a group of spaced-apart microbeams. An imaging panel can be supported by the tubular member diametrically opposite the beam receiver. The plurality of shielded modules are positioned adjacent one another and arranged so that the tubular members of the shielded modules are coaxial along an axis. Rollers are disposed between each of the plurality of shielded modules and the base so that each of the shielded modules can be rotated about the axis independently of the other shielded modules. An elongated table extends through at least part of each of the plurality of shielded modules.

In some embodiments the tubular member is configured so that the grid module rotates with the tubular member when the grid module is engaged with the tubular member.

In further embodiments each of the shielded modules is configured to absorb radiation having an energy less than 500 kV.

In some such embodiments, each of the tubular members is configured to move selectively between an open position and a closed position.

In still further embodiments, each tubular member comprises a first portion hingedly connected to a second portion.

BRIEF DESCRIPTION OF THE DRAWINGS

FIG. 8 is a side view of an embodiment of a patient applicator 80;

FIG. 9A shows the patient applicator 80 of FIG. 8 arranged in a first position;

FIG. 9B shows the patient applicator 80 of FIG. 8 arranged in a second position;

FIG. 22 shows yet another embodiment of a filter layer comprising fan structures and blocks supported on a lattice; and FIG. 23 shows still another embodiment of a filter layer comprising fan structures and a block supported on a lattice.

DESCRIPTION

As will be discussed in more detail below, the present specification discloses apparatus and methods for using superficial radiotherapy (SRT) machines for subcutaneous radiotherapy in a manner that reduces toxicity to healthy tissues while delivering an effective radiotherapy dose to a target tissue. Such apparatus and methods can be effective for treating subcutaneous tissues suffering from inflammation disorders such as joint arthritis and lung inflammation due to COVID-19, as well as cancer tumors. In use, an SRT machine can generate an open-field X-ray beam that is then spatially fractionated into a group of spaced-apart microbeams. This group of microbeams is directed at a target body part. Although a significant proportion of the kilovoltage (<100 kV) and/or orthovoltage (100-500 kV) superficial radiation is absorbed by the skin and adjacent tissue, a significant proportion is also absorbed by the target tissue. And since the beam is spatially fractionated skin toxicity is minimized. After a first therapy pass, the SRT machine is repositioned and a second radiotherapy pass is performed from a different direction. As such, skin and adjacent tissues in the beam path are each subjected to only a single spatially fractionated radiation dose, but the target tissue is subjected to multiple doses.

Various embodiments of patient applicator 80s can be used to support the target body part and receive the group of microbeams during therapy passes. Since only comparatively low-energy X-ray beams are used, shielding requirements are minimized, and thus a patient applicator 80 can be fully shielded yet remain mobile and easily portable, as can the SRT machine. Also, patient applicator 80s can be tubular and thus easily repositioned by simply rotating the tubular patient applicator 80. The associated beam emitter and a grid module 70 that fractionates the beam can rotate with the patient applicator 80 during such repositioning.

Figure 1:
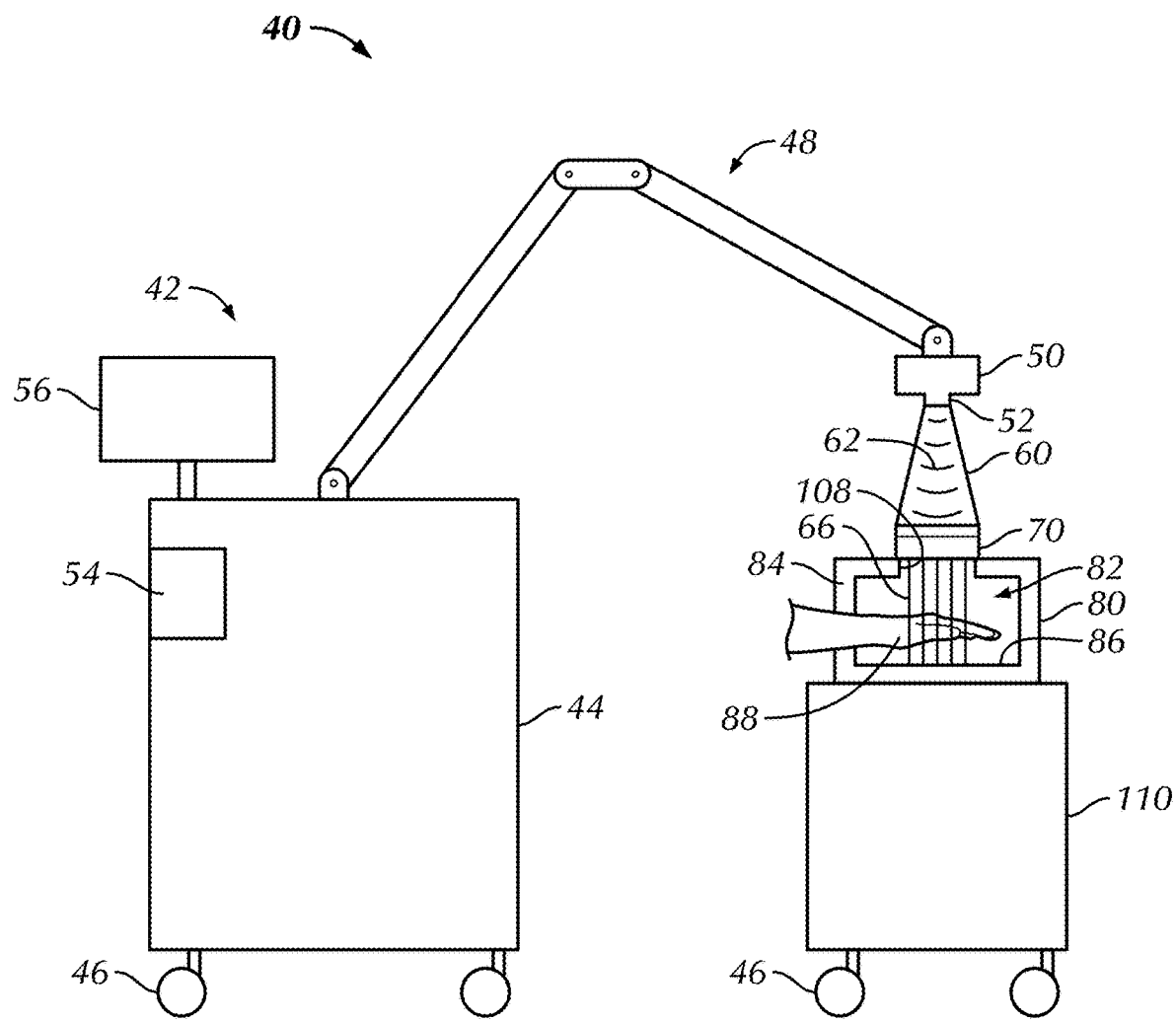
FIG. 1 is a schematic view of a radiation treatment system configured in connection with an embodiment.

With initial reference to FIG. 1, a radiotherapy treatment system 40 is depicted configured in accordance with one embodiment. In the illustrated embodiment a mobile superficial radiotherapy treatment (SRT) machine 42 is provided. The illustrated SRT machine 42 comprises a body 44 supported by wheels 46. A head 50 of the SRT machine 42 is movably connected to the body 44 via an articulating arm structure 48, and is configured so that the head 50 can be selectively placed and held at a broad range of positions relative to the body 44. The head 50 is configured to be a source of X-rays, which can selectively be emitted through an output port 52. Such X-rays are configured to be of an energy level consistent with superficial radiotherapy, such as within a kilovolt (<100 kV) or orthovolt (100-500 kV) energy range.

A processor 54 can be supported within the body 44 and can be configured to control operation of the head 50, particularly output of the head 50. An interface, including a monitor 56, can provide and receive control information to and from a user. In some embodiments the SRT machine 42 can be a standard, commercially available device such as the SRT-100 machine currently available from Sensus Healthcare.

Figure 2:
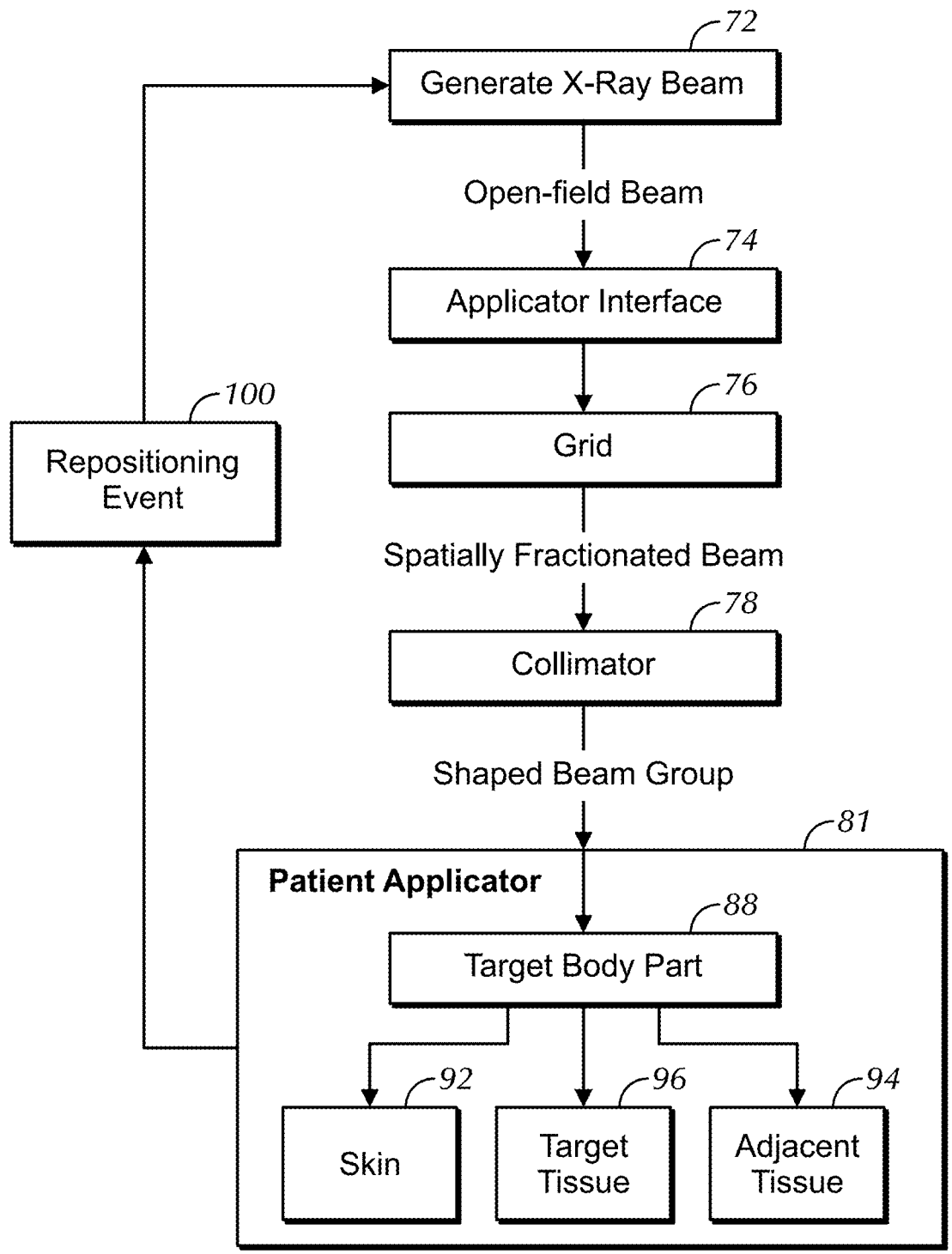
FIG. 2 is a flow chart describing a method of using the radiation treatment system of FIG. 1.

With continued reference to FIG. 1 and additional reference to FIG. 2, the illustrated embodiment comprises an applicator interface 60 that has a proximal end configured to be attached to the output port 52 of the head 50 so as to receive an open-field X-ray beam 62 from the head 50 of the SRT machine 42 and conduct it distally along the length of the applicator interface 60. The applicator interface 60 can be cone-shaped so as to gradually increase in diameter moving towards its distal end. A grid module 70 can be attached to the distal end of the applicator interface 60. The grid module 70 can include one or more grid-shaped filters configured to spatially fractionate the open-field X-ray beam 62 into a group of multiple, spaced-apart microbeams 66. The grid module 70 can also include a collimator configured to define an outer limit or shape of the beam group. In operation the SRT machine 42 generates 72 the open-field X-ray beam 62, which is delivered 74 from the head 50 to the applicator interface 60, which in turn delivers 76 it to the grid module 70 in which the beam is spatially fractionated and can be collimated 78.

The grid module 70 can be attached to or engaged with a patient applicator 80 so that the shaped group of microbeams 66 is supplied 81 to the interior of the patient applicator 80. The patient applicator 80 can include an interior space 82 defined within one or more shielded walls 84. A patient support surface 86 within the patient applicator 80 can be configured to support at least a target body part 88 of the patient to be treated. In the illustrated embodiment the patient applicator 80 is configured to receive a patient's hand upon the patient support surface 86 within a target zone aligned with the beam path. The patient support surface 86 can be configured so that the hand (or other body part) rests directly upon the patient support surface 86. A custom-molded treatment facilitator can be created to correspond to the patient's target body part-here a hand. The treatment facilitator can be secured in place on the patient support surface so as to facilitate patient comfort and/or holding still.

In operation, the collimated microbeam group is directed 90 at the patient's targeted body part within the patient applicator 80. As can be expected with kilovoltage-range energy X-rays, a substantial proportion of the beam energy is absorbed 92 by the patient's skin and adjacent tissue 94, but substantial beam energy is also absorbed by the target tissue 96 intended to be treated by the radiotherapy. By dividing the open-field beam into a plurality of spaced-apart microbeams, absorption of energy, particularly by the skin, is dispersed so that portions of the skin that absorb radiation are spaced between portions of the skin that are substantially unexposed to such radiation. This approach, often referred to as creating "skin islands", has the effect of minimizing damage to the patient's skin.

With continued reference to FIG. 2, after a radiotherapy pass of a target body part 88 from a first position, such as directing the microbeam group at the back of the patient's hand as depicted in FIG. 1, a repositioning event 100 can take place. In the repositioning event, the head, patient applicator 80, and/or patient's target body part 88 can be repositioned for a second therapy pass. For example, in the arrangement shown in FIG. 1, the orientation of the patient's hand within the patient applicator 80 can be reversed so that the open side of the patient's hand faces the grid module 70. A second radiotherapy pass can then be conducted, in which the head 50 generates 72 an open-field X-ray beam 62 that is conducted 74 by the applicator interface 60 to and through grid module 70, which fractionates 76 and collimates 78 the beam and directs 81 the resulting microbeam group 66 into the patient applicator 80 to be absorbed 90 by the target body part 88. Beam energy in the second radiotherapy pass is absorbed 92 by a different portion of the patient's skin and surrounding tissues 94 than absorbed beam energy in the first treatment pass. Importantly, however, beam energy is directed to and absorbed 96 by the target tissue 88 on both radiotherapy passes. As such, the dose of radiation received by the target tissue 88 is maximized and focused on the target tissue 88, but radiation delivery to skin and surrounding tissues is distributed and kept below levels that would be excessively toxic.

Figure 3:
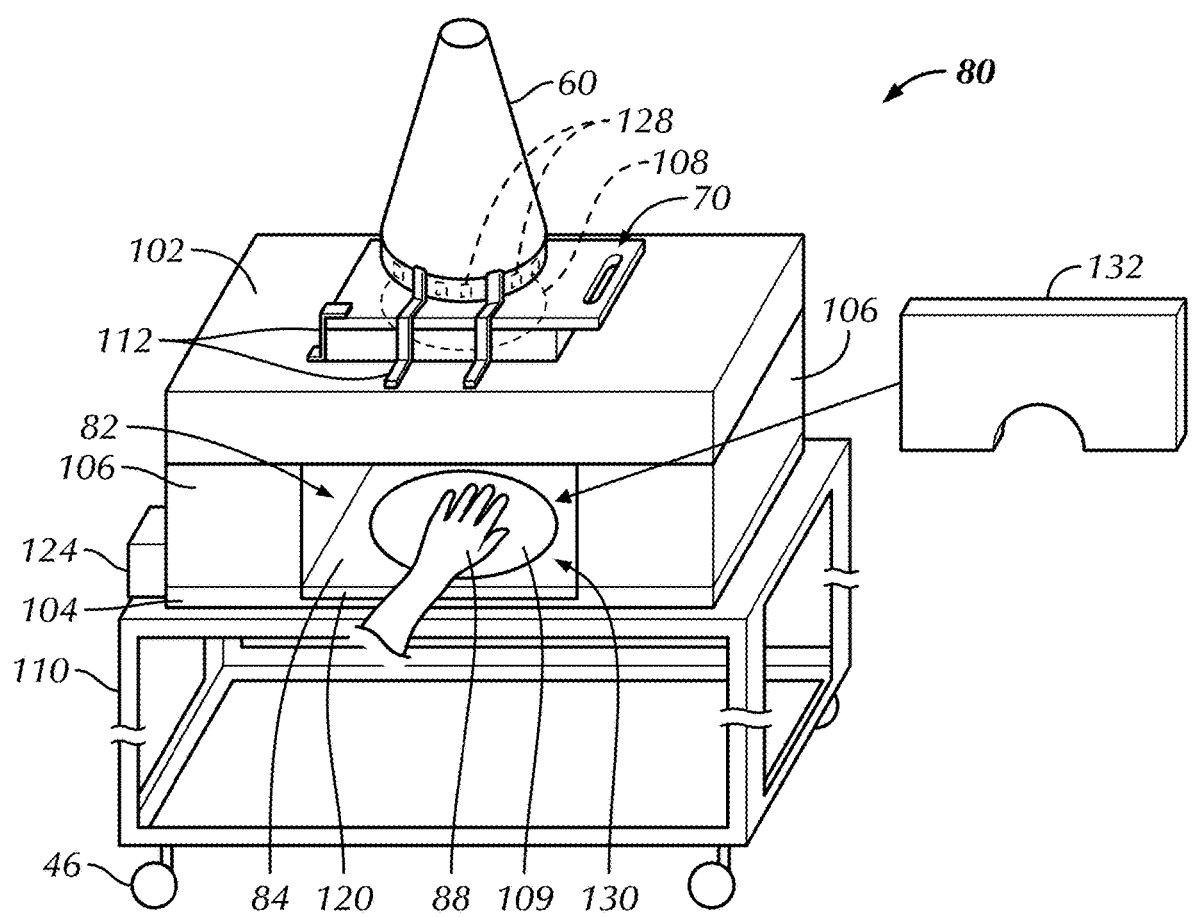
FIG. 3 is a perspective view of a patient applicator 80 portion of the radiation treatment system of FIG. 1.

With reference next to FIG. 3, the patient applicator 80 embodiment that is also shown in FIG. 1 can have an interior space 82 defined by a top wall 102, bottom wall 104 and side walls 106, each of which include sufficient shielding to absorb X-ray energy of the sort emitted by the SRT machine. A receiver aperture 108 can be formed through the top wall 102. The applicator interface 60 and grid module 70 can be positioned and/or supported by the top wall 102 and aligned with the receiver aperture 108 so that the collimated beam group 66 can be directed therethrough and at the target area 109 defined on the support surface 84 defined within the interior space 82. The patient applicator 80 can be sized and configured to be portable. For example, in some embodiments it can be selectively placed on a table. In the illustrated embodiment the patient applicator 80 can be supported on a wheeled table 110 and can thus easily be transported.

In the illustrated embodiment, a plurality of guides 112 extend upwardly from the top wall 102 of the patient applicator 80. The illustrated guides 112 are configured to slidably receive the grid module 70 so that the grid module 70 is releasably held in a desired, repeatable position atop the patient applicator 80 and aligned with the receiver aperture 108. Upper portions of the guides 112 can be configured to receive and support the distal end of the applicator interface 60 to, similarly, releasably hold the applicator interface 60 in a desired, repeatable position immediately adjacent the position of the grid module 70. In this embodiment, once the grid module 70 and applicator interface 60 are in place, either structure can be removed and replaced without disturbing the position of the other relative to the patient applicator 80.

Continuing with reference to FIG. 3, the support surface 84 within the interior space 82 is configured to support a patient's target body part 88. The patient applicator 80 can include an imaging panel 120 opposite the support surface 84 from the receiver aperture 108. The imaging panel 120 is configured so that an imaging dose of an X-ray beam directed at the target body part 88 from the applicator interface 60 facilitate imaging of the target body part 88 prior to radiotherapy. Such imaging can help to better identify and locate the target tissue to be treated by radiotherapy. In the illustrated embodiment the imaging panel 120 also defines the support surface 84, although in other embodiments the imaging panel 120 can be spaced from the support surface 84.

In some embodiments a control module 124 can be attached to the patient applicator 80. The control module 124 can be configured to provide power and to receive a digital signal with imaging data as received by the imaging panel 120. The control module 124 can be configured to be connected via a wired or wireless connection to the SRT machine 42, and thus can communicate imaging data to the SRT processor 54.

As depicted in the embodiment of FIG. 3, in some embodiments a plurality of LEDs 126 can be disposed about the circumference of the applicator interface 60, preferably at or adjacent the distal end thereof. Power for the LEDs 126 can be applied by various structures, including via the control module 124. For example, wires or circuitry from the control module 124 can be configured to apply a low voltage across a pair of the guides 112 of the patient applicator 80, which guides can engage electrodes disposed on the applicator interface 60 that are connected to a circuit including the LEDs 126. As such, the control module 124 can selectively deliver electric power to the LEDs 126. Control of such power delivery can be determined locally at the applicator interface 60 or at the patient applicator 80 control module 124, or remotely, such as by the SRT controller 54 in response to instructions received by an operator. The LEDs 126 can light up the interior space 82 of the patient applicator 80 and thus aid placement of the target body part 88 appropriately on the support surface 84.

An access 130 opening formed through one of the side walls 106 enables the target body part 88 to enter the patient applicator 80 for placement. In some embodiments a portion of the side wall 106 is configured to be removable to create the access opening 130. In further embodiments a second access opening can be provided through another side wall to accommodate treatment of certain target body parts, such as a knee, in which access to the target body part may necessitate adjacent body parts (i.e., upper and lower legs) extending out of opposite sides of the patient applicator 80. Prior to treatment, an access shield 132 can be placed to substantially close the access opening 130. In some embodiments the access shield 132 can be a shielded wall portion with a cavity shaped to fit the portion of the patient's body extending out of the access opening. In additional embodiments the access shield 132 can comprise a flexible lead shielded portion, similar to a lead blanket, that can be shaped to fit around the patient's body part 88 and close the access opening 130. In this manner, the patient applicator 80 can be fully self-contained in providing shielding for the radiotherapy treatments without relying on separate shielding applied either to the patient or to the walls of the room in which the SRT machine 42 is being used.

In the illustrated embodiment the grid module 70 can be slid out of the way so as to not be interposed between the distal end of the applicator interface 60 and the receiver aperture 108. As such, the grid module 70 can be slid out of place so as to not interfere with X-ray imaging and/or to enable light from the LEDs 126 to light up the interior space 82 of the patient applicator 80 during placement of the target body part 88. Once placement and imaging is complete, the grid module 70 can be slid into place so as to be interposed between the applicator interface 60 and the patient applicator 80.

Figure 4:
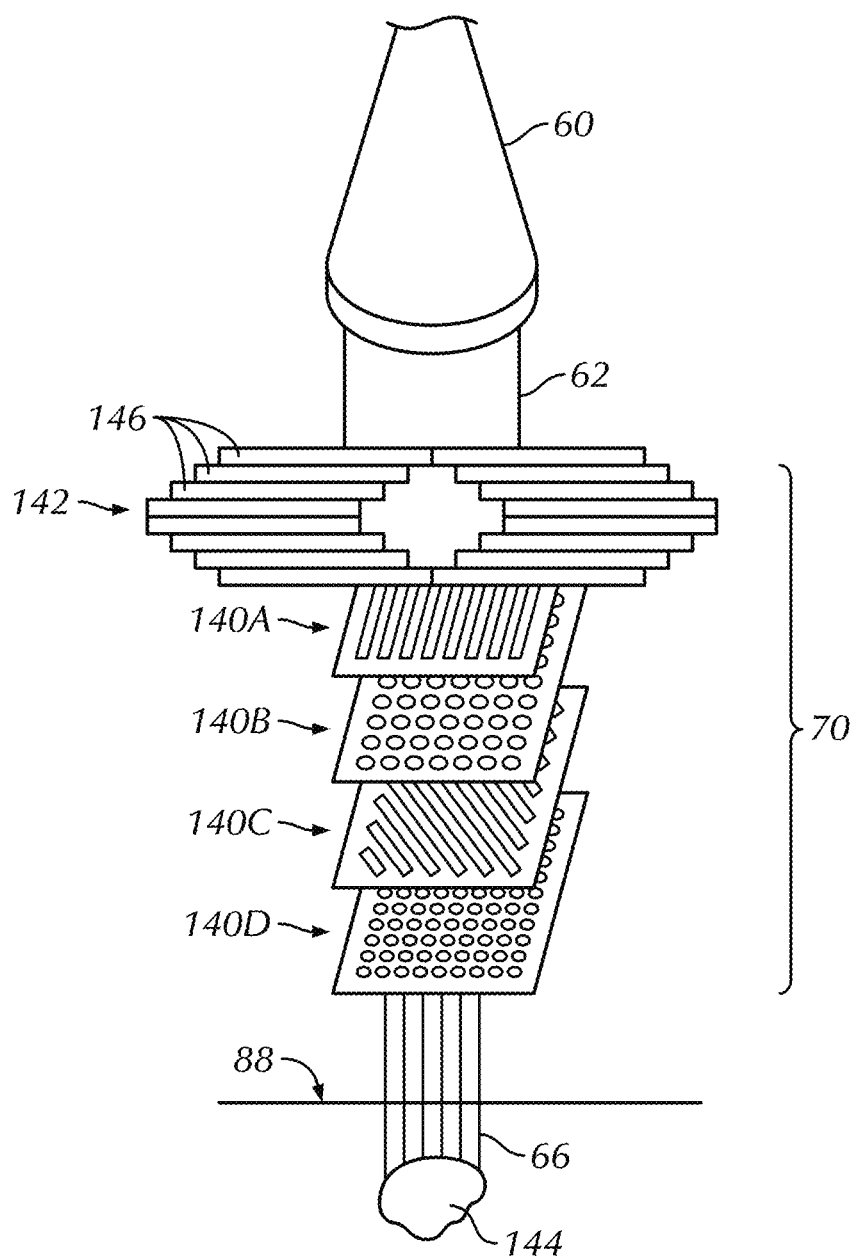
FIG. 4 is a schematic perspective view showing spatial fractionating of an open-field X-ray beam using components of a grid module 70 in accordance with an embodiment.

With reference next to FIG. 4, the grid module 70 can comprise one or more filter members 140 configured to spatially fractionate the open-field X-ray beam received from the head via the applicator interface 60. The grid module 70 can also comprise a collimator 142 configured to shape a perimeter of the beam as desired, and preferably to match the perimeter of the target tissue 144. The illustrated collimator 142 comprises a multi-leaf collimator in which several independently-movable leaves 146 can be moved longitudinally so that the ends of the leaves 146 collectively approximate a desired beam perimeter. Each leaf 146 has shielding properties so as to block X-rays from passing through the leaf 146 so that the resultant beam is limited to pass through the collimator 142 only in the open space between the leaf ends. As such, the beam group will have a perimeter resembling perimeter of the target tissue.

The illustrated grid module 70 comprises a plurality of filter members 140, each with a different filtering configuration. For example, filter member 140A comprises a plurality of elongated slits, and thus fractionates the beam to represent the slit shapes. Filter member 140B comprises a plurality of apertures having a first diameter. As the beam slit shapes pass through filter member 140B the beam becomes further fractionated into pencil-shaped beams. Filter member 140C also includes elongated slots, but such slots are directed diagonally relative to the slots in filter member 140A, and provides further fractionation, or shaping, of the beam group. Filter member 140D comprises a plurality of apertures having a second diameter that is different from the first diameter. The filter members 140 and collimator 142 all work together to spatially fractionate the open-field X-ray beam 60 received as input to the grid module 70 into a collimated beam group 66 comprising a plurality of microbeams sized and configured as desired. Such collimated beam group 66 is directed to the target body part 88 and preferably is absorbed by the target tissue 144. Stray or reflected portions of the X-ray beam will be absorbed by the shielding built into the patient applicator 80. In the embodiment illustrated in FIG. 4, the collimator 142 is positioned upstream of the filter members 140. It is to be understood that in other embodiments the collimator 142 can be disposed downstream of the filter members 140 or interposed between filter members.

Figure 5:
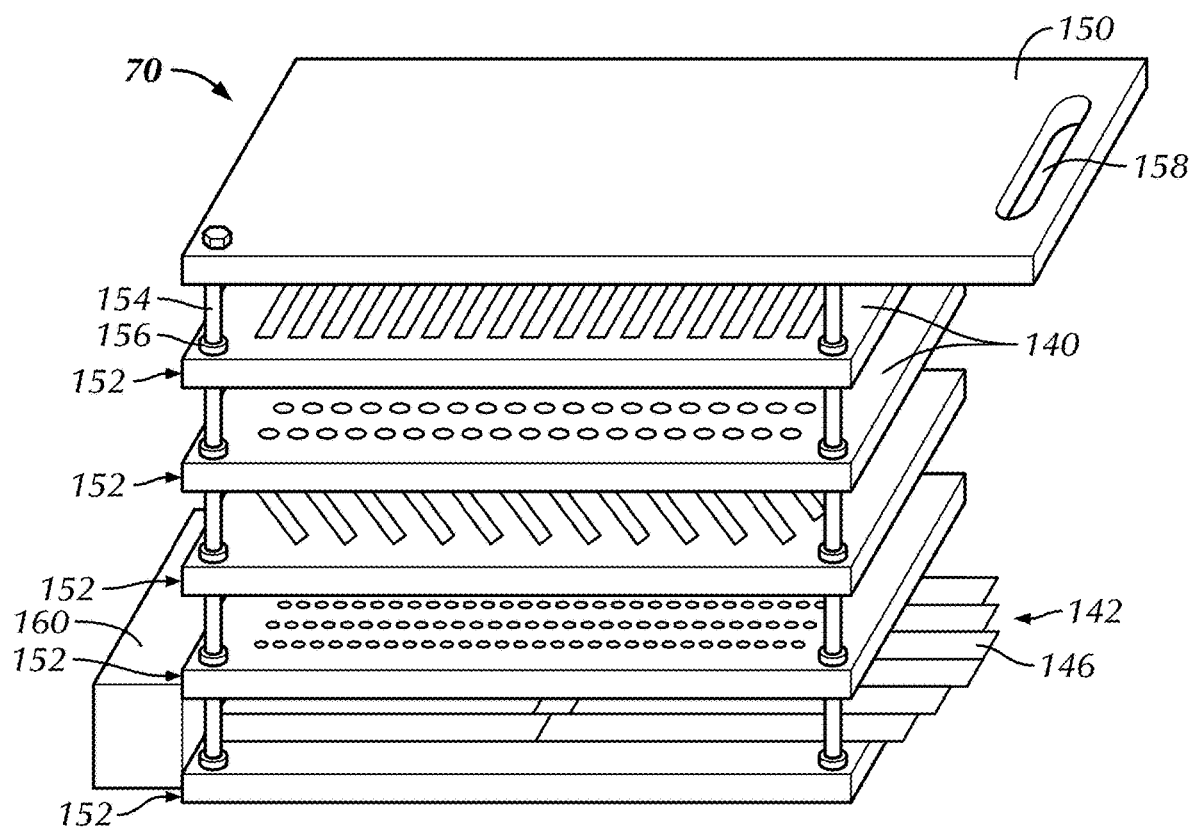
FIG. 5 is a perspective side view of an embodiment of a grid module 70.

With reference next to FIG. 5, in one embodiment, a grid module 70 can comprise a support body 150 to which is attached a plurality of layers 152, each layer comprising a filter member 140 or collimator 142. A connection structure of the illustrated grid module 70 comprises a plurality of shafts 154, or in some instances bolts, that extend through the layers and the support member 150 so as to connect the layers 152 and support member 150 to move together as a unit with the positions of the filters 140 relative to one another remaining fixed. In the illustrated embodiment spacers 156 on the shafts 154 hold each filter member 140 both aligned as desired with and spaced from the adjacent filter member 140. It is to be understood that, in additional embodiments, the adjacent filter members 140 can be stacked directly upon one another. The illustrated support member 150 preferably is somewhat larger in footprint than the filter members, 140 and can have a handle 158 formed thereon so as to facilitate easy carrying and manipulation of the grid module 70.

Figure 6A:
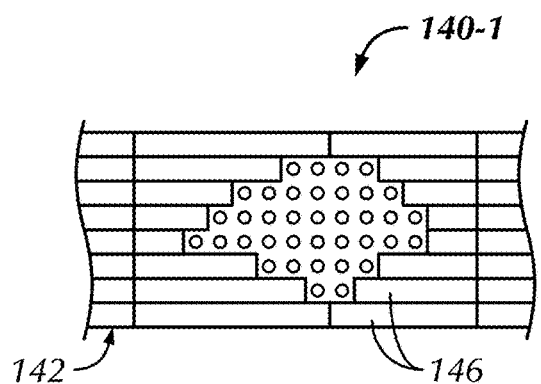
FIG. 6A shows one embodiment of a filter member for use in a grid module 70.
Figure 6B:
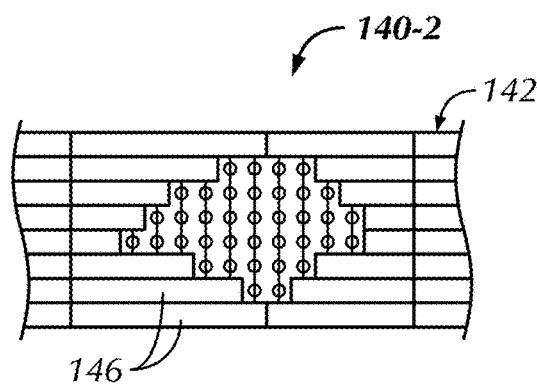
FIG. 6B shows another embodiment of a filter member for use in a grid module 70.
Figure 6C:
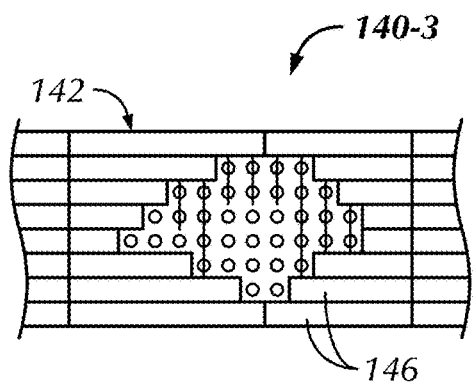
FIG. 6C shows another embodiment of a filter member for use in a grid module 70.
Figure 6D:
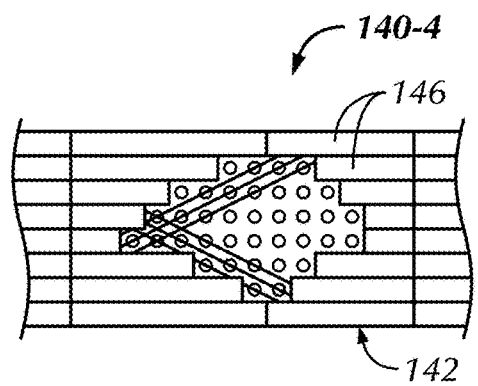
FIG. 6D shows another embodiment of a filter member for use in a grid module 70.

It is to be understood that filter members 140 can be configured in several ways as desired. For example, with reference to FIG. 6A, a filter member 140-1 comprises a consistent small aperture pattern that is uniform throughout. And as shown the collimator 142 covers and blocks the apertures that are outside of the desired treatment perimeter. As shown in FIG. 6B, a filter member 140-2 can incorporate multiple shaping aspects, such as the array of apertures coupled with elongated and parallel slits extending through and between the apertures. FIG. 6C shows an embodiment of a filter member 140-3 in which the elongated and parallel slits extend through only a selected group of the apertures. This configuration will create a beam group in which the microbeams in some portions of the beam group are more densely packed and differently-shaped than microbeams in other portions of the beam group. FIG. 6D shows yet another embodiment of a filter member 140-4 in which only some of the apertures are also joined by slits, the slits are not all parallel, and some apertures are in fact joined by multiple slits. Thus, multiple subgroups of microbeams having various shapes and properties can be created. It is to be understood that many variations of filter member configurations can be employed so as to achieve the desired microbeam pattern for effective treatment in each particular instance, which can include minimizing exposure to certain organs at risk that may be disposed adjacent the target tissue.

Individual leaves 146 of the multi-leaf collimator 142 discussed above in connection with FIGS. 4 and 5 can be moved into a desired position manually by a user so as to define the outer perimeter shape of the group of microbeams. In additional embodiments, however, and with reference again to FIG. 5, a motorized actuator 160 (shown schematically) can be carried on the grid module 70 and configured to automatically adjust the leaves 146 so as to define the microbeam group perimeter shape. In some embodiments the collimator actuator 160 can be linked to, powered by and controlled by the patient applicator 80 control module 124, which in turn can receive instructions from the SRT machine processor 54 as to how to control the collimator 142.

Figure 7:
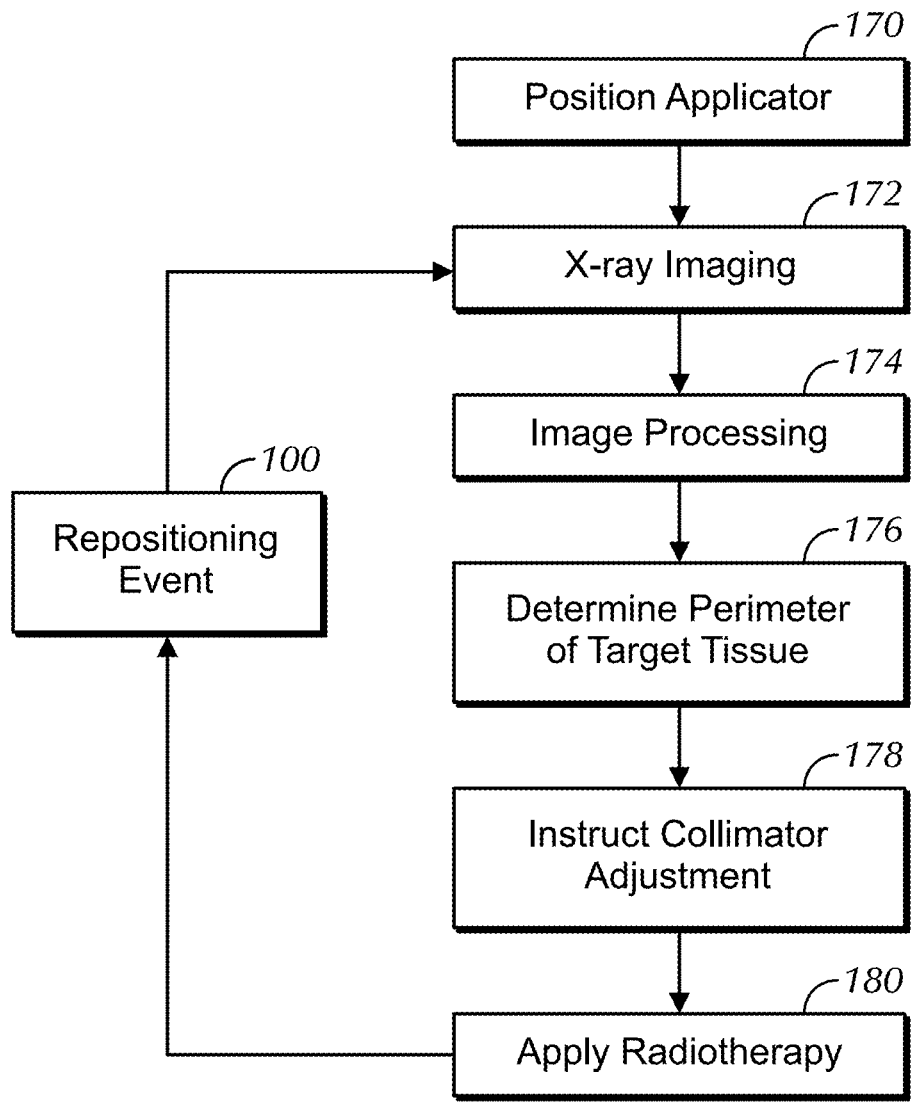
FIG. 7 is a flow chart describing a method of radiotherapy using a patient applicator 80 in accordance with one invention.

In some embodiments a clinician will set the desired perimeter shape using the SRT machine processor 54, or can download such perimeter shape from a previously-stored electronic file obtained from previous imaging. With reference next to FIG. 7, determination of collimator shape settings can also be based on real-time imaging data. For example, once the patent target body part 88 and applicator interface 60 are in position 170, the SRT machine processor 54 can direct that an X-ray image 172 be taken, which image will be captured by the imaging panel 120 and communicated to the SRT machine processor 54. Software accessed by the processor 54 can be configured for image processing so as to analyze 174 the image data and determine 176 the shape and location of the target tissue 144, such as a tumor and/or arthritic joint, as seen from the direction of the applicator interface 60. This shape and location determination operation can be automated by the software, but preferably is subject to correction and/or modification by the user. In other embodiments the user can manually analyze the imaging data to determine the desired outer perimeter.

Once the desired outer perimeter of the treatment beam is determined, the grid module 70 can be put into place, and a signal sent from the SRT machine processor 54 communicating instructions to the collimator actuator 160 to adjust 178 the collimator 142 to define the desired beam group outer perimeter. A radiotherapy pass 180 can then be performed, in which a treatment dose of SRT radiation is generated as an open-field X-ray beam that is communicated from the head 50 to and through the applicator interface 60 to and through the grid module 70, where the open-field beam is fractionated, and further to the target body part 88. After the radiotherapy pass 180 a repositioning event 100 can be performed to change the position of target body part 88, such as to move a patient's hand from a palm-down orientation to a palm-up orientation. The process can be performed again starting with X-Ray imagine 172 so as to determine the correct outer perimeter of the repositioned target tissue 144 based on imaging data and to adjust the collimator to define such correct outer perimeter in order to perform a second radiotherapy pass 180. It is to be understood that, depending on treatment plans and needs, such steps of repositioning, adjusting, and performing another radiotherapy pass can be repeated as many times as clinically indicated. Also, and as discussed in some embodiments that will be presented below, the step 100 of repositioning can involve moving the head, applicator interface 60, and grid module 70, and in some cases the patient applicator 80, rather than moving the patient body part 88.

In the embodiments discussed above, the grid module 70 is supported by the patient interface 80. In additional embodiments the grid module 70 can be configured to be supported by, and to move with, the applicator interface 60, such as being attachable to the distal end of the applicator interface 60. In still further embodiments the grid module 70 can be incorporated into the applicator interface 60 upstream of the distal end of the applicator interface, and individual components, such as individual filter members 140, can be selectively slid into and out of the X-ray path within the applicator interface 60. Preferably, shielding is provided as part of, or even releasably attached to, the applicator interface. Also, preferably the applicator interface and associated structure is lightweight enough to be supported by the articulating arm structure 48 of the SRT machine 42.

It is to be understood that a plurality of grid module 70s can be employed, and can be interchanged for different therapy passes. In some embodiments, a first grid module having filter members arranged in a first configuration can be developed for use for treatment passes from a first direction, in which perhaps the only organ at risk (OAR) is the patient's skin. However, for radiotherapy passes from a different direction a second grid module having filter members arranged in a second configuration can be developed and arranged to customize the microbeam pattern. For example, the second grid module can be configured with smaller holes and no elongated slits in an area anticipated to deliver radiation through a particular OAR. Such a configuration may further spare that OAR from exposure to radiation, but still deliver some dose to the target tissue, which delivered dose will be supplemented by the first pass or additional passes. Preferably such grid modules can be easily swapped out between treatment passes. Additionally, as mentioned above, a grid module can be as simple as a single filter member or as complex as several differently-configured filter members stacked adjacent one another in the beam path.

While some grid modules can incorporate a collimator, in some embodiments one or more collimators can be supported elsewhere on the apparatus. Still further, some multileaf collimators can also incorporate apertures, and thus also perform a spatial fractionization function such as are performed by more typical filter members. And in other embodiments a multileaf collimator can itself have multiple layers of leaves. A first layer of leaves may include apertures so as to function as a filter member and perform spatial fractionation over a portion of the filter/beam shape, while a second layer of leaves may be solid so as to clearly define the outer perimeter of the microbeam group as discussed in embodiments above. In this manner, for example, a single grid module can be used for multiple treatment passes from different directions in which different OARs are at play and can be easily, and even automatically, adjusted between passes. For example, for the second therapy pass, the first layer of leaves may be advanced to reduce the volume of microbeams (and thus reduce the dose) in a pathway through the OAR, while the second layer still defines the outer perimeter of treatment of the target tissue.

With reference next to FIG. 8, another embodiment of a patient treatment device 190 for use with an SRT machine is presented. In the illustrated embodiment, the applicator interface 60 can attach to the output port 52 of the head 50 and the grid module 70 attaches to the applicator interface 60 as discussed above. A patient applicator 80 comprises an offset body made up of a first portion 192 and a second portion 194. The first portion 192 attaches to the grid module 70 and extends in a direction transverse to the X-ray beam longitudinal axis A. Preferably the first portion includes a receiver aperture 108 or is formed of a material that does not interfere with X-rays. The elongated first portion 192 changes direction to also extend for some distance in the longitudinal direction, and joins with the second portion 194, which continues in the longitudinal direction, but then is redirected transversely so as to eventually intersect the longitudinal axis A of the beam and align with the grid module 70. An imaging panel 120 can be integrated into the second portion 194 so as to intersect the beam longitudinal axis A and thus be in the beam pathway. A working space 196 is defined within the first and second portions 192, 194.

The illustrated first portion 192 and second portion 194 can generally follow a curving arcuate path around an axis of curvature that intersects the beam longitudinal axis A. In additional embodiments, however, various specific shapes can be employed to create the working space. Additionally, in the illustrated embodiment, a telescoping part 198 of the second portion 194 is telescopically received within the first portion 192 and can be held in place using a fastener 199 and/or ratcheting mechanism so as to adjust the distance between the grid module 70 and the imaging panel.

Continuing with reference to FIGS. 8 and 9A-B, the applicator interface 60, grid module 70 and patient applicator 80 preferably are supported by and move together with the head 50 of the SRT machine 42. In use, a patient can relax upon a support surface 84 such as on a table 200 or bed, and the patient treatment device 190 can be moved relative to the bed 200 so that the patient and bed 200 are disposed within the working space 196 as depicted in FIG. 9A. A first therapy pass can be taken in this first position. Without moving the patient, the head 50 can be repositioned so that the rest of the patient treatment device 190 rotates about the patient target body part to a second therapy pass position and direction as depicted in FIG. 9B. Features such as the distance between the grid module 70 and imaging panel 120 can be adjusted as desired based on factors such as the width of the patient body part at the second position, or other factors. Multiple therapy passes from multiple positions and directions can be performed so as to deliver repeated radiotherapy doses from multiple therapy passes to the target tissue but limit radiation exposure to skin and other OARs to the dose of a single therapy pass. Notably, in at least some embodiments the patient need not move or reposition themselves between therapy passes, as the patient applicator 80 can be moved for the repositioning event. Also, although this embodiment is shown being used with a patient lying upon a bed 200, it is anticipated that this embodiment of the patient treatment device 190 can also be used with other support surfaces in which only a target body part, such as a knee, wrist or the like, need be disposed on the support surface 84.

Figure 10:
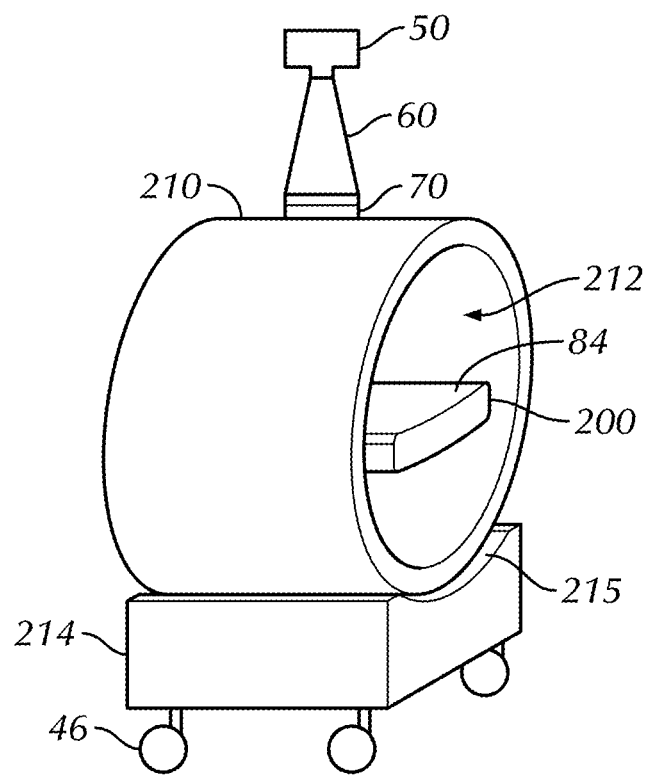
FIG. 10 is a perspective view of another embodiment of a patient applicator 80.
Figure 11:
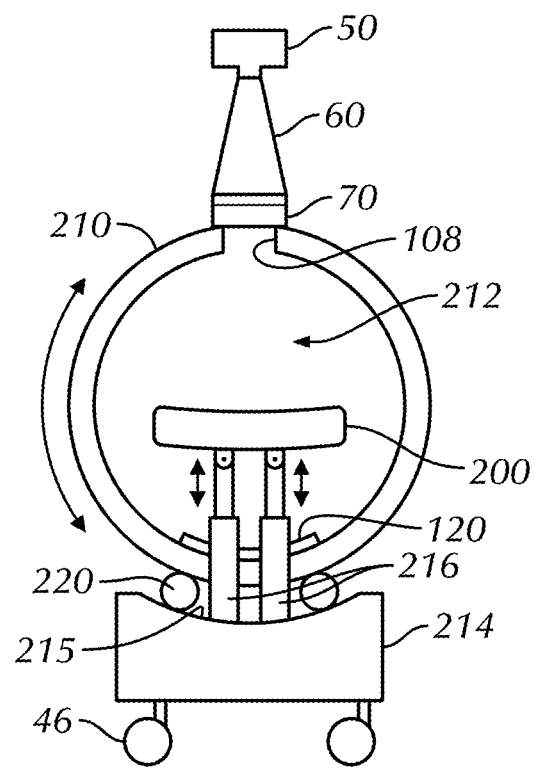
FIG. 11 is an end view of the patient applicator 80 of FIG. 10.

With reference next to FIGS. 10 and 11, in another embodiment, a patient applicator 80 comprises a tubular member 210 having a substantially circular cross-section. An interior space 212 is defined within the tubular member 210. The tubular member 210 is supported by a wheeled base 214. A surface 216 of the base is arcuate and includes one or more roller bearings 220 configured so that the tubular member 210 can rotate over the base 214. Preferably a rotation lock enables a user to lock the tubular member 210 in position when a desired rotation position is reached. The tubular member 210 can include shielding sufficient for absorbing X-rays generated by the SRT machine 42. A receiver aperture 108 is defined through the tubular member 210, and a grid module 70, applicator interface 60 and SRT machine head 50 can be attached to the tubular member 210 in a manner to be aligned with the receiver aperture 108. An image panel 120 can be provided generally diametrically opposite the receiver aperture 108. A table 200 defining a patient support surface 84 extends through, or at least within, the interior space 212. In the illustrated embodiment the table 200 is supported by adjustable supports 216, such as telescoping supports, that enable the table 200 to be raised or lowered as desired. The illustrated adjustable supports 216 can be independently adjusted to, for instance, tilt the table 200 if desired.

In the embodiment illustrated in FIGS. 10 and 11, a patient can rest a target body part on the patient support surface 84 of the table 200. The clinician can set up the system to perform a first therapy pass at a first position, such as shown in FIG. 11. After the first therapy pass, the tubular member 210 can be rotated. The grid module 70, applicator interface 60, and SRT machine head 50 can remain attached to the tubular member 210 during such rotation. When the desired direction for a second therapy pass is reached, the tubular member 210 can be locked into place and the second therapy pass performed. If it is desired to take a second therapy pass at a direction that is blocked by the attached equipment (applicator interface 60, et al.) contacting the base 214, the table 200 can be tilted in order to take the therapy pass at that desired direction. The shielding in the walls of the tubular member 210 provides sufficient containment of X-rays.

Figure 12:
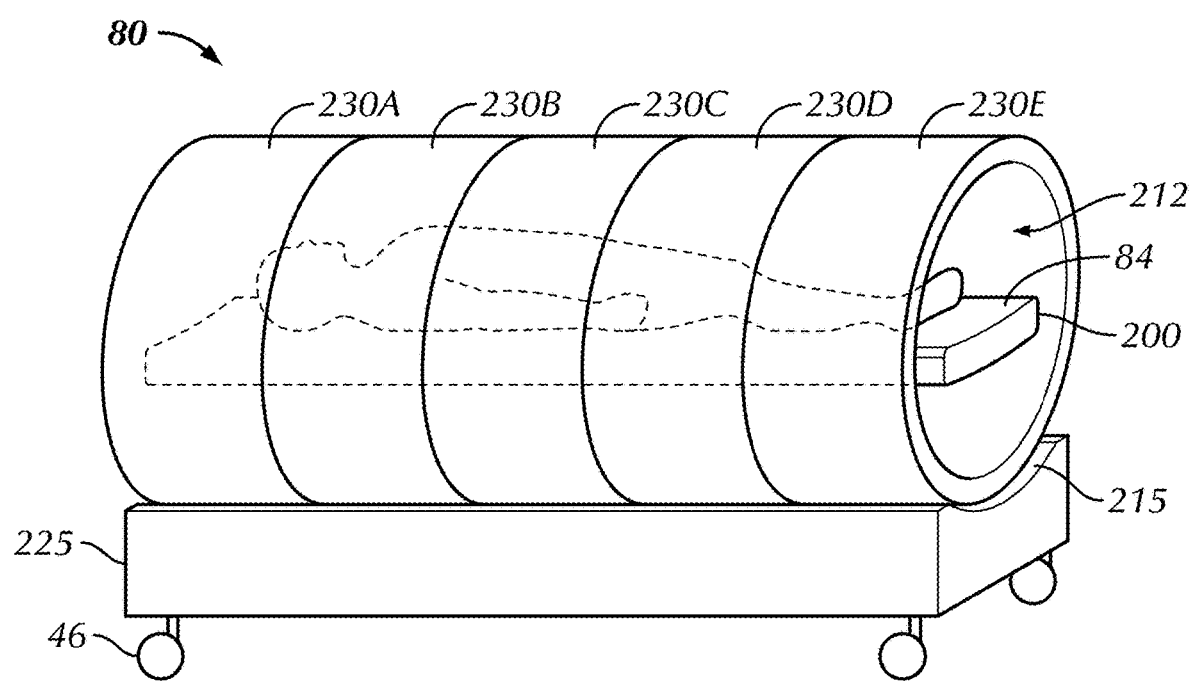
FIG. 12 is a perspective view of yet another embodiment of a patient applicator 80 employing a plurality of shielded modules.

With reference next to FIG. 12, a schematic view of an embodiment of a modular shielded patient applicator 80 is depicted. The modular shielded patient applicator 80 comprises an elongated table 200, such as a bed, supported on a wheeled base structure 225. A plurality of shielded modules 230 are also supported by the wheeled body structure 225 and are configured to generally encircle the table 200. Each illustrated shielded module 230 is generally tubular in shape, with a circular cross-section. In one embodiment the shielded modules 230 are formed of a leaded glass configured to effectively function as a shield for SRT machine-level X-rays. In some embodiments, each of the shielded modules 230 can be moved longitudinally relative to other modules. As such, to provide radiotherapy to, for example, inflamed lung tissue due to COVID-19 or a cancerous lesion at or around the patient's lungs, shielded modules 230A and 230B can be moved longitudinally in a first direction while modules 230C, 230D and 230E are moved in the opposite direction so as to provide a space aligned with the patient's chest. A treatment device, such as the treatment device 190 configuration discussed above in connection with FIGS. 8 and 9, can then be used to provide treatment. Separate shielding, such as leaded blankets, can be provided around the patient treatment device, but with the remaining shielded modules 230A-E in place, sufficient shielding remains in place to safely perform the therapy. In another embodiment, any one of the shielded modules 230 can be removed to provide space for such radiotherapy.

With continued reference to FIG. 12 and additional reference to FIG. 10, in another embodiment, each of the shielded modules 230 can be configured similar to the tubular member 210 discussed in connection with FIG. 10 so that each of the shielded modules 230 can be used to take therapy passes and operated independently of the other shielded modules 230.

Figure 13:
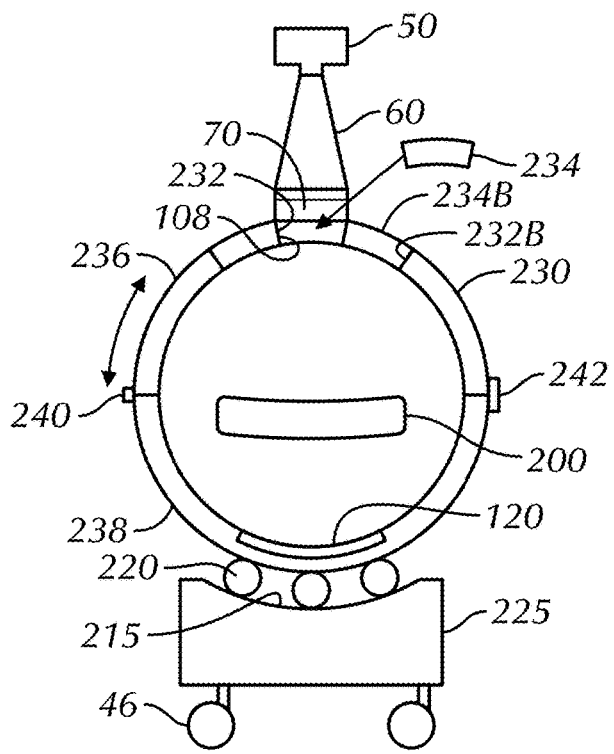
FIG. 13 is an end view of one embodiment of a shielded module.

With continued reference to FIG. 12 and additional reference to FIG. 13, in another embodiment, each shielded module 230 can be used as a patient applicator 80, and can stay in place, with its associated shielding, during use. FIG. 13 depicts a cross-section of one of the shielded modules in which a cutout 232 is provided. Typically a plug 234 fits within the cutout 232, but the plug 234 can be removed to define a receiver aperture 108 through the shielded material (which can be leaded glass). The cutout 232 is sized to correspond to an applicator interface 60 and grid module 70. In some embodiments, the grid module 70 can be sized and shaped to fit into and be held within the cutout 232. An image panel 120 can be provided opposite the cutout 232. An applicator interface 60 and grid module 70 can be attached in a manner to provide a beam path from the applicator interface 60 to the imaging panel 120, and the collective shielded modules 230 provide sufficient shielding during radiotherapy.

In the illustrated embodiment the shielded modules 230 are tubular, with a circular cross-section, and can be attached to the base 225 by bearings 220 so that each circular shielded module 230 can be rotated. Preferably a rotation lock is provided to hold the shielded module 230 in place when a desired rotational position is reached. In this manner a first therapy pass can be performed while the shielded module 230—and connected SRT machine head 50, applicator interface 60 and grid module 70, are disposed at a desired rotational position. The shielded module 230, with the applicator interface 60 still attached, can then be rotated to a second desired rotational position, at which a second therapy pass can be performed. Since all of the shielded modules 230 remain in place throughout the process, sufficient shielding is provided without the need to add any additional shielding during therapy passes. In this manner, the illustrated modular shielded patient applicator 80 can be fully self-contained, providing its own shielding while being movable to a desired treatment location.

Preferably the table 200 is supported so that it can be moved up and down so as to accommodate desired positions and distances from beam generation to patient skin. Also, preferably the table 200 is configured to be tiltable so that treatment passes can be performed at rotational positions relative to the table in which the shielded module 230 would otherwise be blocked from further rotation by the applicator interface 60 contacting the base structure 225.

As shown in FIG. 13, additional cutouts 232b of multiple sizes can be provided, with corresponding plugs 234b. And in fact cutout 232 can be formed within the plug 234b of a larger cutout 232b. As such, the shielded module 230 can be used with various sizes of X-ray emitters, applicator interface 60s and grid module 70s.

In some embodiments, and as shown in FIG. 13, the shielded module 230 can be divided into a first portion 236 and a second portion 238 that are connected via a hinge 240 and latch 242. As such, the shielded module 230 can be moved from the illustrated closed configuration to an open configuration by releasing the latch 242 and rotating the first portion 236 about the hinge 240. This can provide access to the inside of the shielded module 230 to make adjustments, access the patient, enable the patient to climb onto the table 200 or be transferred from a gurney, or as otherwise needed. Preferably the roller bearings 220 are placed so as not to interfere with the hinge 140 and/or latch 142 as the shielded module 230 is rotated.

Figure 14A:
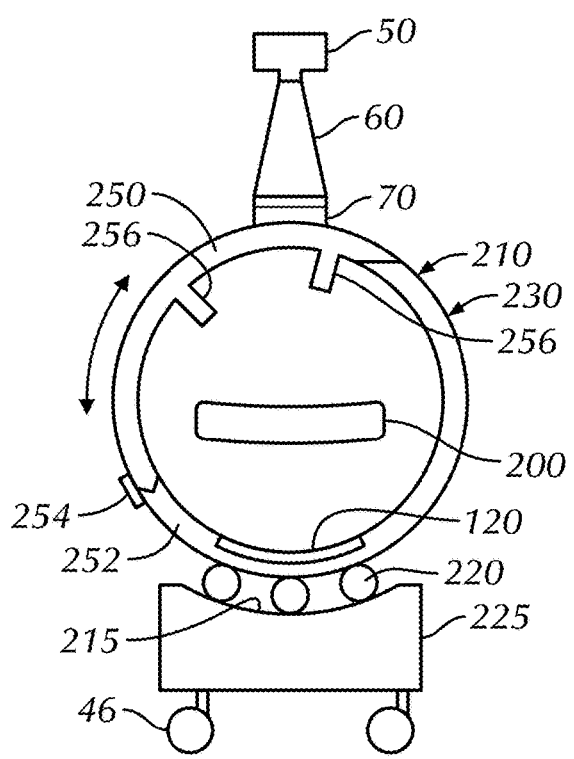
FIG. 14A is an end view of another embodiment of a shielded module, shown in a closed configuration.
Figure 14B:
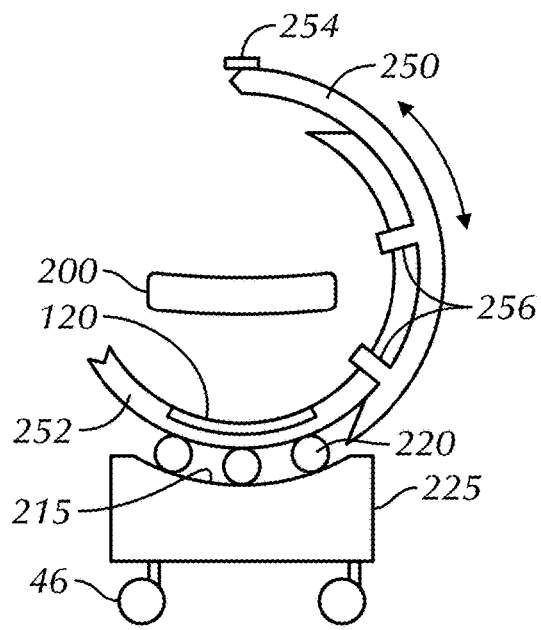
FIG. 14B shows the shielded module of FIG. 14A in an open configuration.
Figure 15:
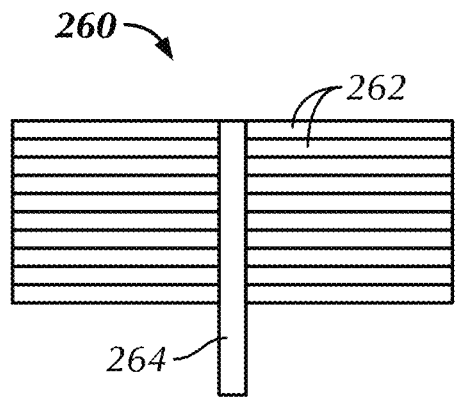
FIG. 15 is a side view of an embodiment of a fan structure.

With reference next to FIGS. 14A and B, a patient applicator 80 can have a shielded module 230 that can be opened without a hinge. For example, the tubular member 210 of the shielded module 230 can be made up of a first portion 250 and a second portion 252 that, when fit together in a closed configuration as shown in FIG. 14A, define the tubular member 210 that can rotate upon the base 225. A latch 254, and other hardware as desired, can maintain the first and second portions 250, 252 engaged with one another securely in the closed position. In order to provide access to the table 200, such as for patient ingress and egress, tubular member 210 can be transitioned to the open configuration shown in FIG. 14B. To accomplish this, the latch 254 can be released and the first member 250 pushed so that it shifts over the second member 252 and can be rotated over the outer surface of the second member 252. Guides 256 along the edges of the tubular member 210 can engage the second member 252 and facilitate the first member 250 translating along the outer wall of the second member 252. Excessive movement of the first member 250 can be blocked by the base 225 and or a stop structure as desired. Once the need for access has passed, the first member 250 can be pulled back into place and the latch 254 and/or other structure secured.

In embodiments employing a modular shielded patient applicator 80, the table 200 can be supported in any of a variety of desired manners. In one embodiment the table is supported at its ends and outside of the shielded modules 230, such as by being connected to the base structure 225 at both ends. In some embodiments the table 200 can be at least partially retracted so that the patient can easily climb onto or be moved onto the table. In additional embodiments the table can be supported by supports that extend from the table to the base structure between adjacent shielded modules 230. In still further embodiments the table 230 can be at least partially supported by the interior surfaces of the shielded modules 230. Such support can be by a static connection in which the table is rigidly attached to an associated shielded module, or by an adjustable connection, such as a lockable roller. In some embodiments the table 200 can be rollable between shielded modules 230. Thus, if, for example, it is desired to make therapy passes using a selected shielded module, the table can be moved so as to be supported by an adjacent shielded module so that the selected shielded module is free from any connection to the table that could interfere with operation.

In some embodiments the base structure 225 can extend long beyond the shielded modules 230 so that the table 200 can be fully removed from the shielded modules for patient ingress and egress. In additional embodiments, as discussed above, the shielded modules can open so as to allow patient ingress and egress. In hybrid embodiments the table can partially exit the shielded modules, and a subset of the shielded modules can open to accommodate patient ingress and egress.

Embodiments of the grid module 70 discussed above have included layers comprising filter members. In some embodiments additional, actively-adjustable structures can also be incorporated into a layer of the grid module 70 to participate in performing the spatial fractionation of the beam. Such a layer can be combined with other filter layers within the grid module 70.

Figure 16A:
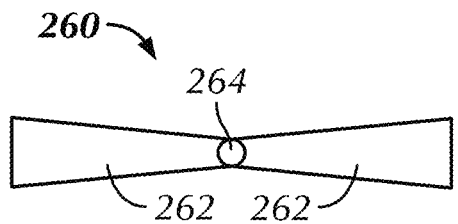
FIG. 16A is a top view of the fan structure of FIG. 15.
Figure 16B:
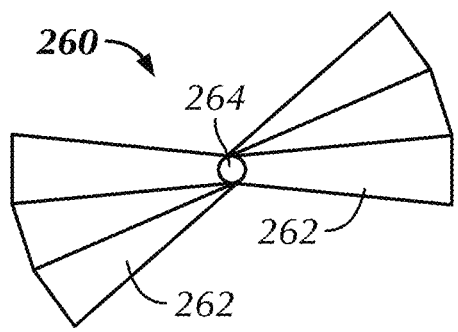
FIG. 16B is a top view of the fan structure of FIG. 16A partially deployed.
Figure 16C:
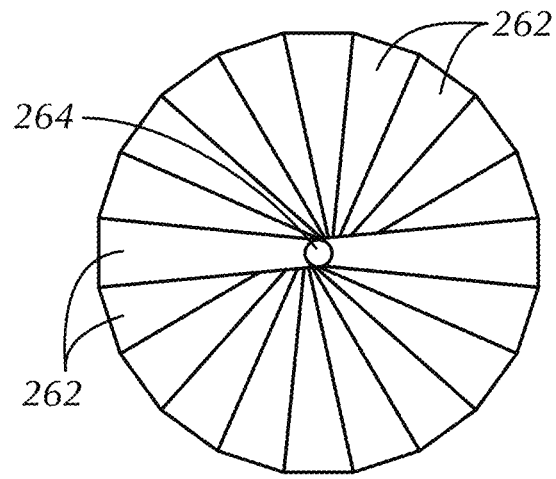
FIG. 16C is a top view of the fan structure of FIG. 16A fully deployed.

With reference next to FIGS. 15 and 16A-C, a fan structure 260 can comprise a plurality of stacked elongated fan blades 262 attached to a rotatable rod 264. The fan structure 260 is configured to deploy by being unfurled as the rod 264 is rotated, not like a conventional hand fan. Each blade 262 is limited in rotation relative to the adjacent blade 262, such as by an overlapping ridge or stop structure limiting the relative movement between adjacent blades, and/or by a textile connection between blades 262. Thus, as the rod 264 is rotated and the fan begins to unfurl as depicted in FIG. 16B, the blades 262 unfurl one at a time and stop when unfurled relative the adjacent blade 262. Eventually, and as depicted in FIG. 16C, the fan structure 260 can be fully unfurled, and a generally circular shape is formed. Of course, if the rod 264 stops rotating midway through the unfurling process, the fan 260 will not be fully deployed, and will not complete a circle.

Figure 17A:
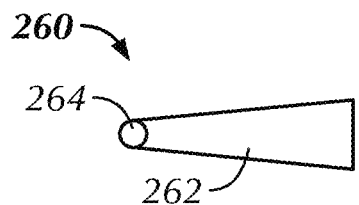
FIG. 17A is a top view of another embodiment of a fan structure.
Figure 17B:
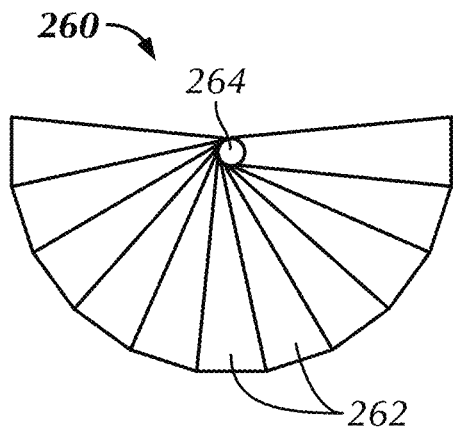
FIG. 17B is a top view of the fan structure of FIG. 17A fully deployed.

In the embodiment illustrated in FIGS. 15 and 16A-C, elongated blades 262 extend in opposite directions from the rod 264. With additional reference to FIGS. 17A-B, another embodiment of a fan structure 260 comprises elongated fan blades 262 that extend in only one direction from the rod 264. As depicted, when fully unfurled the fan structure 260 forms a half-circle shape. Of course, depending on the number and size/shape of fan blades 262, the unfurled fan structure 260 can extend less than a half circle, such as 90°, or more than a half circle, such as 135° about the rod 264.

Figure 18:
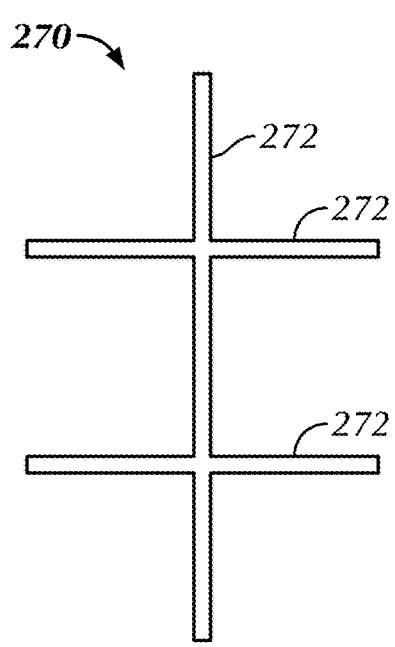
FIG. 18 is a schematic view of an embodiment of a lattice structure configured to support a plurality of fan structures.
Figure 19:
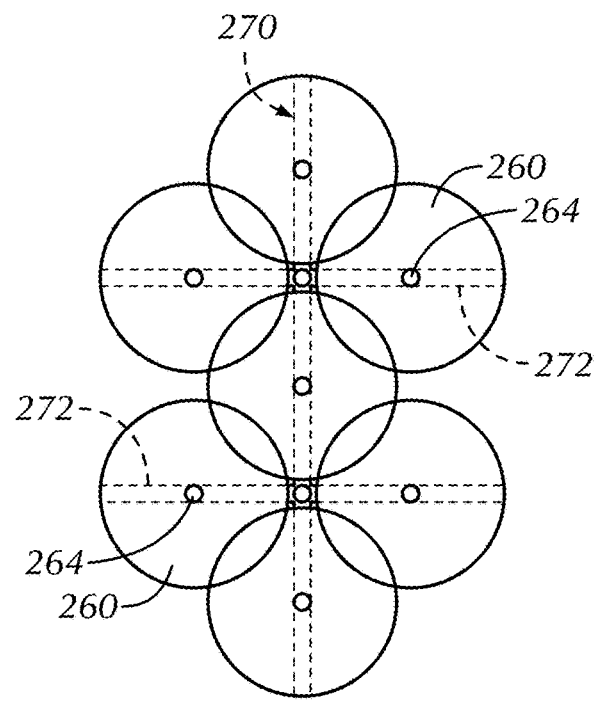
FIG. 19 shows deployed fan structures supported by the lattice of FIG. 18.

With additional reference to FIG. 18, a lattice structure 270 can comprise a plurality of support members 272 configured to rotationally support rods 262 of fan structures 260. For example, with reference next to FIG. 19, an embodiment is depicted in which a plurality of fan structures 260 are supported by the lattice structure 270, and are shown with the fans unfurled, or deployed. In this manner, at least some of the deployed fan structures 260 overlap each other, while gaps remain between others of the deployed fan structures 260. In some embodiments, the lattice 270 and fan structures 260 can be included as a layer of the grid module 70. When deployed, the fan structures 260 block at least some of the X-ray beam, but allow portions of the beam to pass through gaps between adjacent fans 260, similar to the holes or slits provided in filter member embodiments discussed above. Fans can be fully or partially deployed to provide gaps in order to meet desired beam dose and density targets. In some embodiments the rods 264 can be motor- actuated and even independently controlled relative to one another. To wit, in some embodiments the SRT machine processor 54 can direct actuation of the fan structures 54 in order to shape and configure fractionation of the treatment beam as desired for a particular therapy pass.

Figure 20:
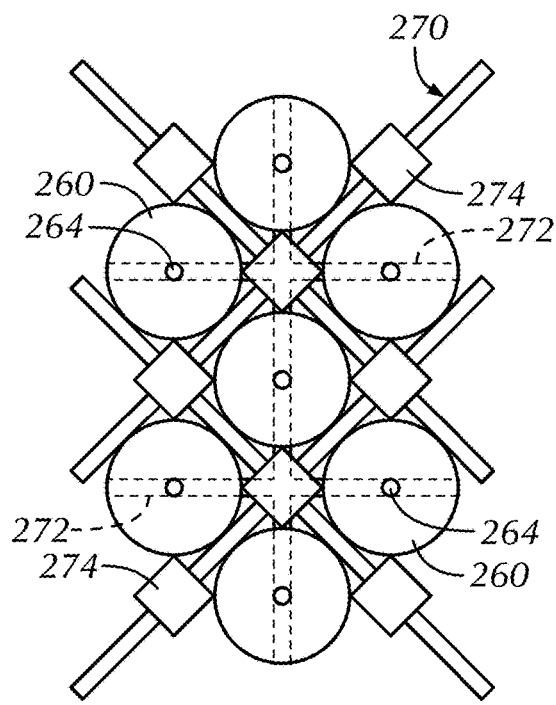
FIG. 20 shows another embodiment of a filter layer comprising fan structures and blocks supported on a lattice.
Figure 21:
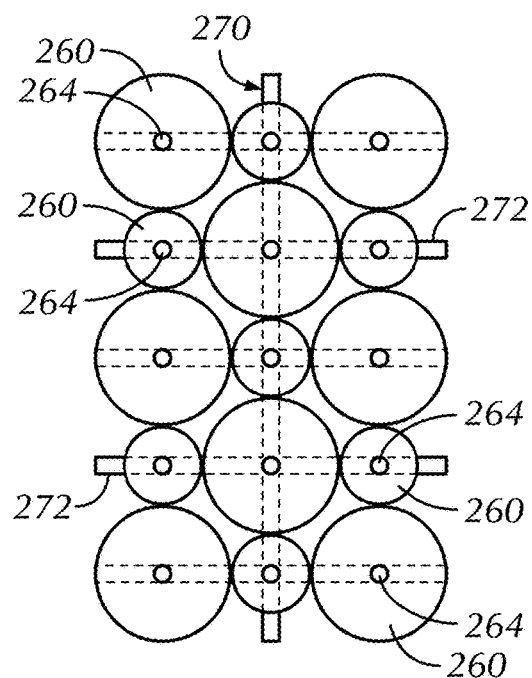
FIG. 21 shows another embodiment of a filter layer comprising fan structures supported on a lattice.

The layer 152 that includes the lattice structure 270 and fan structure 260 can be configured in various ways. For example, with reference next to FIG. 20, diagonal support members of the lattice structure 270 can support a plurality of static blocks 274 that work together with the movable fan structures 260 to block and shape the treatment beam. And as depicted in FIG. 21, fan structures 260 of various sizes can be employed. FIG. 22 depicts a further embodiment in which fan structures 260 are combined with static, non-adjustable blocks 274 that are supported by the lattice structure 270 and form part of the layer 152. FIG. 23 demonstrates an embodiment in which a portion of the layer 152 is fully blocked off, and fan structures 260 forming full circles work together with fan structures 260 forming partial circles to define the layer's filtering shape and performance. Also, it is to be understood that the fans 260 can be of various sizes, and fan blade 262 sizes and shapes within any particular fan can differ so as to create non-circular shapes upon deployment.

It is to be understood that other actively-adjustable structures can be included with layers in the grid module 70 so that the SRT machine processor 54 can direct changes in the grid module 70 performance between therapy passes.

The embodiments discussed above have disclosed structures with substantial specificity. This has provided a good context for disclosing and discussing inventive subject matter. However, it is to be understood that other embodiments may employ different specific structural shapes and interactions.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. For example, principles concerning use of an image panel as discussed in connection with one embodiment can also be employed with other embodiments. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above.

What is claimed is:

1. A method of performing radiotherapy upon a subcutaneous target tissue, comprising:
   directing a first open-field beam of X-rays having an energy less than 500 kV into a grid module, the grid module configured to spatially fractionate the first open-field beam into a first group of microbeams;

directing the first group of microbeams into a patient applicator, the patient applicator having a wall structure defining an interior space and a patient support surface configured to support a target body part;

directing the first group of microbeams at the target body part so that radiation from the first group of microbeams penetrates and is partially absorbed by a first skin zone of the target body part and is also partially absorbed by the target tissue;

repositioning one or more of the grid module and target body part;

directing a second open-field beam of X-rays having an energy less than 500 kV into the grid module so that the second open-field beam is spatially fractionated into a second group of microbeams;

directing the second group of microbeams into the patient applicator; and directing the second group of microbeams at the target body part so that radiation from the second group of microbeams penetrates and is partially absorbed by a second skin zone of the target body part and is also partially absorbed by the target tissue;

wherein the first skin zone is spaced from the second skin zone.

2. The method of claim 1, wherein repositioning comprises moving a portion of the patient applicator while leaving the target body part and patient support surface static.

3. The method of claim 1, comprising actively modifying the grid module prior to directing the second open-field beam so that the second group of microbeams is configured differently than the first group of microbeams.

4. The method of claim 1, comprising obtaining an X-ray image of the target tissue prior to directing the first open-field beam, determining a first perimeter shape of the target tissue and adjusting the grid module so that the first group of microbeams has an outer perimeter shape approximating the first perimeter shape.

5. The method of claim 2, comprising obtaining an X-ray image of the target tissue after the repositioning, determining a second perimeter shape of the target tissue and adjusting the grid module so that the second group of microbeams has an outer perimeter shape approximating the second perimeter shape.

6. A radiotherapy device, comprising:
an applicator interface configured to attach to a head of a superficial radiotherapy machine and positioned so as to receive an open-field X-ray beam from the head;
a grid module configured to attach to the applicator interface and configured to receive the open-field X-ray beam from the applicator interface, the grid module comprising a filter member configured to spatially fractionate the open-field X-ray beam into a group of microbeams having a beam axis; and
a patient applicator attached to the grid module, the patient applicator comprising an applicator body having a first portion that extends in a direction transverse to the beam axis, a second portion that extends in a direction generally parallel to the beam axis, and a third portion that extends in a direction transverse to the beam axis, the third portion having a distal end that intersects the beam axis and is spaced from the first portion;
wherein the third portion comprises an imaging panel.

7. The radiotherapy device as in claim 6, wherein the patient applicator is configured so that a distance between the distal end of the third portion and the first portion can be selectively decreased.

8. A radiotherapy device, comprising:
a wheeled base;
a plurality of shielded modules supported on the base, each of the shielded modules comprising:
a tubular member having a generally circular cross-section;
a beam receiver extending through a wall of the tubular member, the tubular member being configured to selectively engage a grid module at and adjacent the beam receiver, the grid module comprising at least one filter member configured to spatially fractionate an input open-field X-ray beam and output a group of spaced-apart microbeams; and
an imaging panel supported by the tubular member diametrically opposite the beam receiver;
the plurality of shielded modules positioned adjacent one another and arranged so that the tubular members of the shielded modules are coaxial along an axis;
rollers disposed between each of the plurality of shielded modules and the base so that each of the shielded modules can be rotated about the axis independently of the other shielded modules; and
an elongated table extending through at least part of each of the plurality of shielded modules.

9. The radiotherapy device of claim 8, wherein the tubular member is configured so that the grid module rotates with the tubular member when the grid module is engaged with the tubular member.

10. The radiotherapy device of claim 8, wherein each of the shielded modules is configured to absorb radiation having an energy less than 500 kV.

11. The radiotherapy device of claim 8, wherein each of the tubular members is configured to move selectively between an open position and a closed position.

12. The radiotherapy device of claim 11, wherein each tubular member comprises a first portion hingedly connected to a second portion.

* * * * *